United States Patent [19]
Yerkovich et al.

[11] Patent Number: 5,748,427
[45] Date of Patent: May 5, 1998

[54] METHOD AND SYSTEM FOR DETECTING RELAY FAILURE

[75] Inventors: Daniel Yerkovich, Snohomish; Stephen T. Vincent, Redmond, both of Wash.

[73] Assignee: Physio-Control Corporation, Redmond, Wash.

[21] Appl. No.: 770,629

[22] Filed: Dec. 19, 1996

[51] Int. Cl.⁶ .................................................. H02H 3/24
[52] U.S. Cl. ........................................ 361/92; 128/908
[58] Field of Search ............................. 361/56, 78, 86, 361/88, 92, 156, 170, 187, 232; 128/908; 607/5

[56] References Cited

U.S. PATENT DOCUMENTS

| | | |
|---|---|---|
| 3,364,419 | 1/1968 | Anderson . |
| 4,645,886 | 2/1987 | Williams . |
| 4,870,364 | 9/1989 | Trox et al. . |
| 5,097,830 | 3/1992 | Eikefjord et al. . |
| 5,153,522 | 10/1992 | Sano . |
| 5,182,517 | 1/1993 | Thelen et al. . |
| 5,227,729 | 7/1993 | Hoshino . |
| 5,243,291 | 9/1993 | Umemura . |
| 5,285,779 | 2/1994 | Cameron et al. . |
| 5,398,025 | 3/1995 | Herman . |
| 5,455,733 | 10/1995 | Waggamon . |

*Primary Examiner*—Ronald W. Leja
*Attorney, Agent, or Firm*—Christensen, O'Connor, Johnson & Kindness PLLC

[57] ABSTRACT

In an external cardiac defibrillator (8), a method and system for determining when a relay (22) has failed in a conductive state. The defibrillator (8) includes a charge circuit (14) that charges an energy storage capacitor (C) to a predetermined voltage. The relay (22) is closed to direct a defibrillation pulse from the energy storage capacitor to a patient (25) needing ventricular therapy. The relay (22) is then opened following application of the defibrillation pulse. A monitor circuit (18) monitors the voltage on the energy storage capacitor. If the measured voltage across the energy storage capacitor (C) is less than or equal to a threshold value after a predetermined delay, the relay (22) has failed. If the measured voltage exceeds the threshold value, the relay (22) is operating correctly.

20 Claims, 4 Drawing Sheets

METHOD AND SYSTEM FOR DETECTING RELAY FAILURE

FIELD OF THE INVENTION

The present invention relates generally to systems for monitoring a switch for failure, and more particularly, to systems for detecting a relay failure.

BACKGROUND OF THE INVENTION

One of the most common and life-threatening consequences of a heart attack is the onset of ventricular fibrillation. During ventricular fibrillation, the heart of a heart attack victim is unable to pump a sufficient amount of blood required by the victim's body. The conventional treatment to terminate ventricular fibrillation is to apply a strong electric pulse to the victim's heart during ventricular fibrillation. The electric pulse terminates the chaotic activity characteristic of arrhythmias. The termination of such activity restores the normal pumping action of the heart, thereby supplying the necessary blood flow to the victim's body.

To allow treatment of ventricular arrhythmia at an emergency site, portable external cardiac defibrillators have been developed by many manufacturers. Conventional external defibrillators employ the use of an energy storage capacitor and a switching mechanism, typically an electro-mechanical relay, to generate the necessary defibrillation pulse. During operation, the energy storage capacitor is charged to a preselected voltage. After the desired voltage on the energy storage capacitor is attained, a discharge control signal closes the relay. Closing the relay transfers the electric charge stored in the energy storage capacitor to a pair of electrodes. The transferred electric charge takes the form of an electric current pulse, i.e., a defibrillation pulse. The electrodes are positioned on the chest of the patient to most effectively direct the defibrillation pulse. Typically, a wave shaping circuit is also employed in external cardiac defibrillators to achieve the desired shape of the defibrillation pulse. After application of the defibrillation pulse, the relay is opened to disconnect the patient from the energy storage capacitor.

Sometimes the application of a single defibrillation pulse fails to restore the victim's heart to a normal pumping condition. In such an event, it may be necessary to apply an additional defibrillation pulse. To deliver another defibrillation pulse, the energy storage capacitor is again charged to a preselected voltage. When the energy storage capacitor is charged to the desired voltage, the external cardiac defibrillator is ready to deliver a second defibrillation pulse in the manner described above. It will be appreciated that each time a defibrillation pulse is to be generated, it is therefore necessary to close and open the relay.

The proper functioning of the relay is vital to the operation of a conventional external cardiac defibrillator. If the relay fails, then the defibrillator cannot deliver a defibrillation pulse. An undetected relay failure will therefore significantly jeopardize the welfare of the victim.

Several failure modes exist for a relay. In one failure mode, the relay is frozen in a closed position, maintaining a continuous circuit between the energy storage capacitor and the victim. The failure in a closed position may be caused by a mechanical breakdown of the relay components. Alternatively, the failure in a closed position may be due to the relay contacts welding shut. In conventional cardiac defibrillators, the storage capacitor may attain voltages as high as approximately 5 kilovolts. When the relay is closed to deliver a defibrillation pulse, the relay is subject to high current. Although relays in conventional cardiac defibrillators are designed to withstand high currents, extensive use or defects can cause the relay contacts to become welded together when the relay is closed and a defibrillation pulse applied to the patient. Regardless of the cause of the relay being frozen closed, the end result is that the storage capacitor cannot be recharged to apply another defibrillation pulse to the patient. The defibrillator therefore becomes unusable as a treatment device.

Although relays in external cardiac defibrillators ideally should never fail, relays nonetheless can and do fail. When the relay fails, the user of the external cardiac defibrillator should therefore be notified.

Conventional methods to detect relay failure exist but present significant drawbacks and so have not been used in external defibrillators. For example, additional circuitry and a mechanism could be added to detect the location of the armature in the relay. The additional circuitry required to detect the location of the relay armature would add undue complexity, an additional failure mode, and additional cost to a conventional external defibrillator. Moreover, the inclusion of additional circuitry would add weight and increase the size of a conventional cardiac defibrillator. The increased size and weight detracts from the portability of external cardiac defibrillators which, it will be appreciated, should be as small and light as possible. It is not believed that conventional methods of detecting a relay failure have therefore ever been incorporated in an external defibrillator.

SUMMARY OF THE INVENTION

A method and system for detecting the failure of a switching mechanism in an external cardiac defibrillator is provided. The defibrillator includes an energy storage capacitor and a switching mechanism, preferably an electro-mechanical relay. The energy storage capacitor is charged when the relay is open, and discharged during the application of a defibrillation pulse when the relay is closed. A monitor circuit monitors the voltage across the energy storage capacitor after the application of a defibrillation pulse. It has been found that the voltage across the energy storage capacitor will rebound, or increase, following the sudden discharge of the capacitor when the relay is opened after discharge. The voltage rebound across the energy storage capacitor may be used to test the operation of the relay. If the voltage on the energy storage capacitor exceeds a predetermined rebound voltage value, i.e., a threshold voltage, after application of a defibrillation pulse, the relay has returned to the open position and is therefore operating correctly. If the voltage on the energy storage capacitor is equal to or less than the threshold voltage after application of the defibrillation pulse, the relay has failed in a closed position since the rebound voltage across the capacitor is being shunted to the patient.

In accordance with one aspect of the invention, the monitor circuit includes a voltage divider for scaling the voltage measured across the energy storage capacitor. Two amplifiers and corresponding analog-to-digital converters amplify and convert the scaled capacitor voltage into a digital signal indicative of the voltage on the energy storage capacitor. The use of two amplifiers and analog-to-digital converters allows accurate monitoring of the voltage across the energy storage capacitor at both high and low voltages.

Several advantages arise from the method and system for detecting relay failure formed in accordance with this invention. Perhaps most importantly, the method and system simply and accurately identifies when the contacts of a relay have become welded shut or otherwise have failed in a closed position after the application of a defibrillation pulse. The invention provides a simple and reliable technique for identifying relay failure by eliminating the need for electronic components devoted to directly monitoring the position of the relay. Because the extra monitoring components are unnecessary, a system formed in accordance with the present invention and incorporated in a portable cardiac defibrillator reduces the overall cost, size, and weight of the defibrillator.

DETAILED DESCRIPTION OF THE PREFERRED EMBODIMENT

Figure 1:
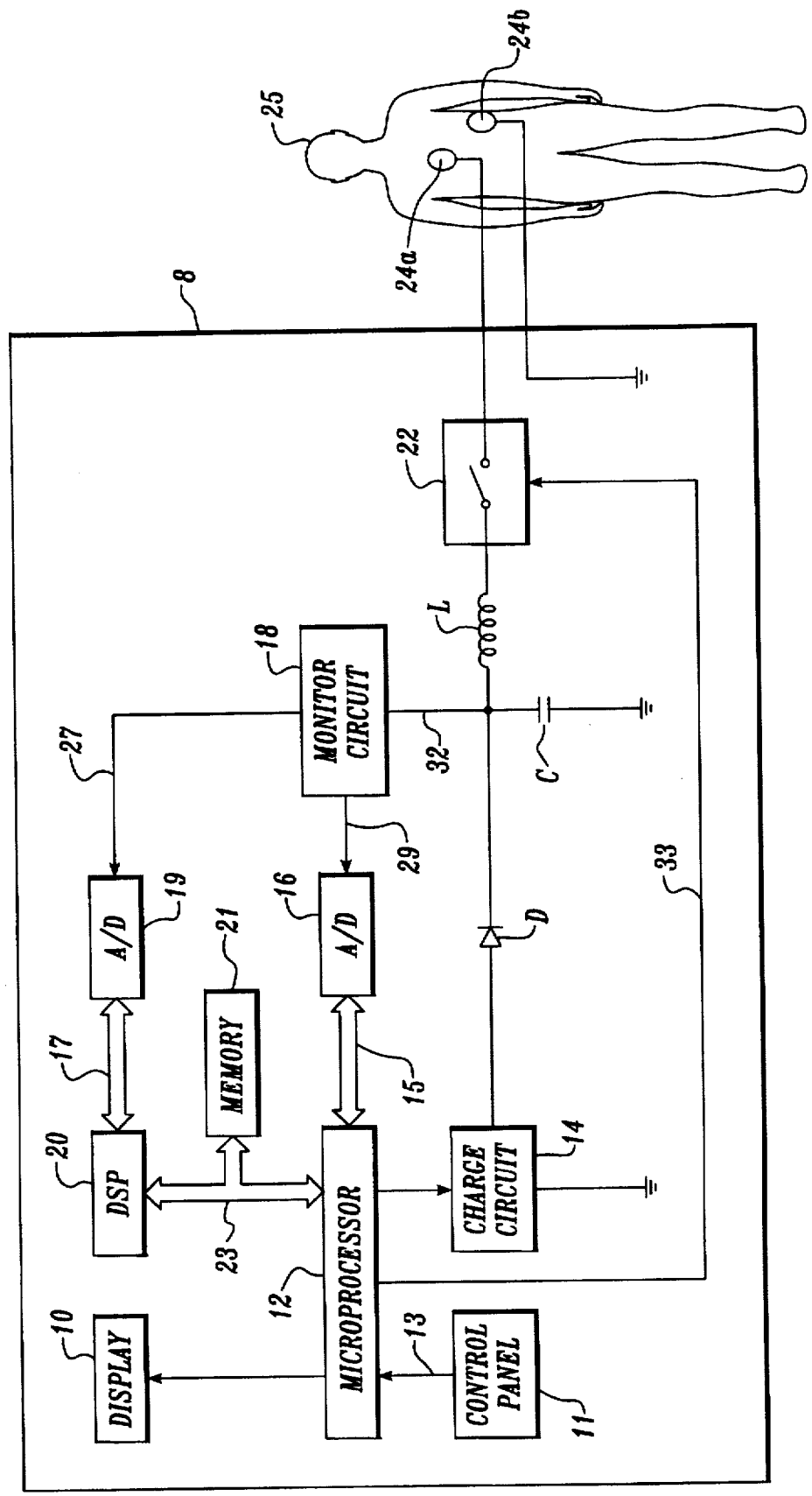
FIG. 1 is a block diagram of a portable external defibrillator incorporating a system for detecting a relay failure formed in accordance with the present invention.

FIG. 1 is a block diagram of a portable external cardiac defibrillator 8 connected to a patient 25. The defibrillator 8 stores electric charge and delivers the electric charge to the patient in the form of an electric current pulse, i.e., defibrillation pulse. The defibrillation pulse is modified to have a particular shape and applied to the patient over a set of electrodes 24a, 24b if the patient is experiencing ventricular fibrillation.

The defibrillator 8 includes a microprocessor 12 that is central to the operation of the defibrillator 8. One function of the microprocessor is to manage the user interface to allow operation of the defibrillator. The microprocessor 12 is connected to a display 10 and a control panel 11. Information is entered on the control panel 11 by a defibrillator operator to control the defibrillator. The display 10 indicates to the operator the condition of the defibrillator 8 and the patient 25.

In one mode of operation, the microprocessor 12 analyzes an electrocardiogram (ECG) of the patient 25 to identify a shockable rhythm. As an ECG signal is received, the microprocessor 12 analyzes and stores the ECG signal as episode data for later use. In this regard, the episode data is transferred by the microprocessor 12 over a bus 23 to a memory 21. If a shockable rhythm is detected, the microprocessor 12 charges an energy storage capacitor C to a desired voltage. Charging the energy storage capacitor C prepares the defibrillator to apply a defibrillation pulse to the patient 25.

To charge the energy storage capacitor C to the desired voltage, the microprocessor 12 is coupled to a charge circuit 14. The charge circuit 14 is connected to the positive lead of the energy storage capacitor C through a diode D. The negative lead of capacitor C is connected to ground. An appropriate command from the microprocessor 12 causes the charge circuit 14 to generate a current that is rectified by diode D and applied to the energy storage capacitor C. The current applied to the energy storage capacitor C causes it to charge. The energy storage capacitor C has a value of 34 microfarads in the preferred embodiment. Capacitor C is preferably charged to a value between approximately 3.0 kilovolts and 5.5 kilovolts, depending on the condition of the patient 25 and other factors such as the energy of the defibrillation pulse to be applied to the patient.

Figure 2:
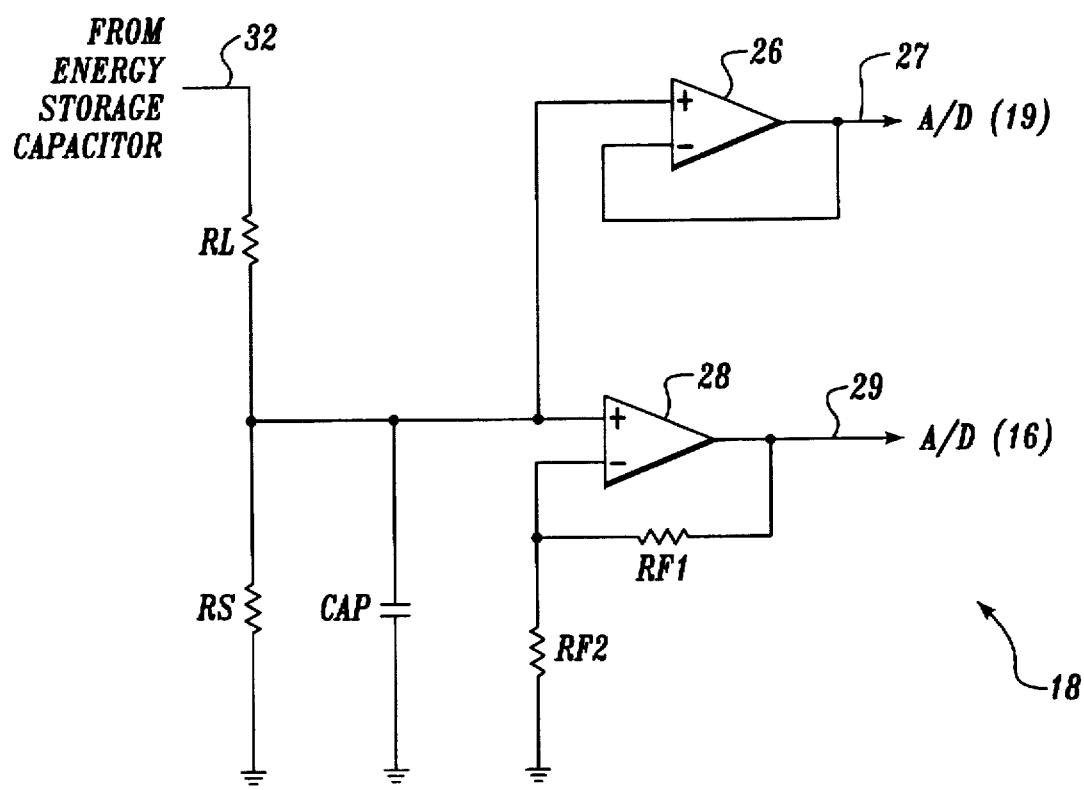
FIG. 2 is a schematic diagram of a monitor circuit suitable for monitoring a voltage across an energy storage capacitor in the external defibrillator.

The voltage across the energy storage capacitor C is monitored by the microprocessor 12 as the capacitor is being charged. To aid in monitoring the voltage on the energy storage capacitor, a monitor circuit 18 is connected to the capacitor by a line 32. A preferred construction of the monitor circuit 18 is shown in greater detail in FIG. 2. As depicted in FIG. 2, a resistor RL and a resistor RS are connected in series between the energy storage capacitor C and ground. Resistor RL and resistor RS form a voltage divider that steps down the high voltage across capacitor C. Accordingly, a scaled voltage appears at the junction between resistor RL and resistor RS. A capacitor CAP is connected in parallel with resistor RS to filter the scaled voltage and remove high frequency noise.

The scaled voltage is applied to the noninverting inputs of two operational amplifiers 26, 28. The first operational amplifier 26 is connected in a unity gain configuration. That is, the inverting input of the operational amplifier is connected to the output of the operational amplifier. The output of the operational amplifier is connected to an analog-to-digital converter 19 by a line 27. The analog-to-digital converter is coupled to a digital signal processor (DSP) 20 by a bus 17. The output of the first operational amplifier 26 is converted from an analog signal to a digital signal by the analog-to-digital converter 19 and provided to the digital signal processor 20. The digital signal processor 20 provides the signal indicative of the voltage on the energy storage capacitor C to the microprocessor 12 via the bus 23, as discussed in additional detail below.

The second operational amplifier 28 is configured to amplify the scaled voltage. The non-inverting input of the amplifier is coupled to ground through a resistor RF2, and to the output of the amplifier through a resistor RF1. Preferably, operational amplifier 28 has a gain of 21. The second operational amplifier 28 amplifies the scaled voltage, and provides the amplified signal to an analog-to-digital converter 16 on a line 29. The signal indicative of the voltage on the energy storage capacitor C is converted from an analog signal to a digital signal by the analog-to-digital converter 16, and provided to the microprocessor 12 on a bus 15.

Those skilled in the art will appreciate that the first operational amplifier 26 and the second operational amplifier 28 convert the scaled voltage to an amplitude that falls within the input range of the corresponding analog-to-digital converter. The first operational amplifier 26 is configured to buffer the scaled voltage corresponding to the maximum charge placed on the energy storage capacitor C. As discussed in additional detail below, the method of detecting a relay failure requires measuring very low voltages across the capacitor. The second operational amplifier 28 is therefore configured to amplify low voltages across the capacitor to a range that allows the voltages to be accurately measured.

As the energy storage capacitor C is charging, the microprocessor 12 receives signals indicative of the measured voltage across the capacitor from the digital signal processor 20. Based on the received signals, the microprocessor 12 determines the actual voltage on the energy storage capacitor C and controls the charge circuit 14 to charge the capacitor to a desired level.

After the voltage across the energy storage capacitor C has reached the desired level, the defibrillator 8 is prepared to deliver a defibrillation pulse. To apply the defibrillation pulse to the patient 25, a normally-open relay 22 is provided in the defibrillator. The relay 22 is preferably an electromechanical relay having an armature that can be switched to connect or disconnect the energy storage capacitor C to the patient 25. One terminal of the normally-open relay 22 is connected to the positive lead of the capacitor C through an inductor L. A second terminal of the relay 22 is connected to the first electrode 24a. The second electrode 24b is connected to defibrillator ground. The relay is connected to the microprocessor 12 by a control line 33. A control signal applied by the microprocessor on the control line causes the relay to switch between the open state, in which the relay does not conduct, and the closed state, in which a conductive path is created between the two relay terminals.

The relay 22 is open during charging of the energy storage capacitor C and closed to apply a defibrillation pulse. The closure of the relay 22 initiates a defibrillation pulse flowing from the energy storage capacitor C, through the inductor L, the relay 22, and the electrode 24a to the patient 25, and via a return path though electrode 24b to ground. The inductor L shapes the defibrillation pulse that is applied to the patient. After the application of the defibrillation pulse, the relay 22 is opened by a control signal from the microprocessor. The opening of the relay 22 allows the energy storage capacitor C to be recharged in the event that another defibrillation pulse is necessary.

Figure 3:
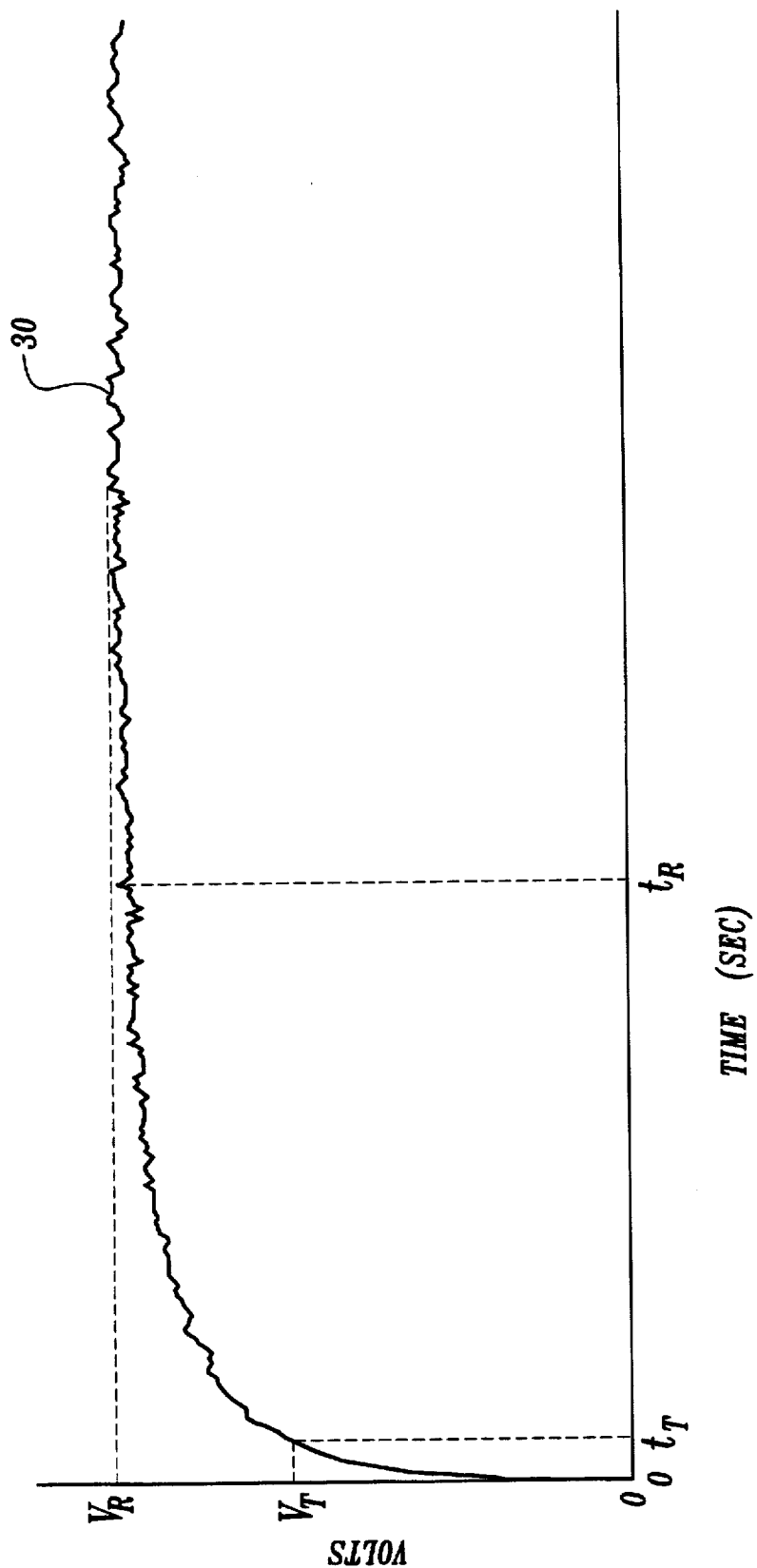
FIG. 3 is a graph illustrating a voltage rebound across the energy storage capacitor after application of a defibrillation pulse.

It has been found that when the relay 22 opens after the delivery of a defibrillation pulse, but before further charging begins, the voltage on the energy storage capacitor C will rebound from a value equal to or near zero to an approximately constant voltage (hereinafter the "rebound voltage"). FIG. 3 illustrates the voltage across the energy storage capacitor C as a function of time after the relay 22 has opened following application a defibrillation pulse. The abscissa indicates the passage of time measured in seconds after the relay 22 has opened. The ordinate represents the voltage on the energy storage capacitor C measured in volts. Line 30 therefore represents the voltage across the energy storage capacitor C as a function of time. When the time is near or equal to zero seconds, the voltage on the energy storage capacitor is approximately equal to zero. Immediately following the opening of the relay, the voltage on the capacitor rises exponentially and eventually settles at an approximately constant rebound voltage $V_R$. The rebound voltage $V_R$ is reached at a rebound time $t_R$.

The rebound phenomenon of the energy storage capacitor is believed to be in part caused by dielectric absorption, i.e., the ability of a capacitor to continue generating internal charging currents that are delayed following a sudden discharge of electric current. The energy storage capacitor may be simply modeled as a capacitor $C_O$, equivalent to the value of the energy storage capacitor, in parallel with the series connection of an internal dielectric resistance $R_d$ and an internal dielectric capacitance $C_d$. The output voltage in the time domain is then roughly modeled by the following equations:

$$V_{out}(t) = V_o \left( \frac{C_d}{C_o + C_d} \right) (1 - e^{\frac{-t}{\tau}}) \quad (1)$$

$$\tau = R_d \frac{C_d C_o}{C_d + C_o} \quad (2)$$

where:
$C_O$=energy storage capacitor value;
$C_d$=modeled dielectric capacitance;
$R_d$=modeled dielectric resistance;

$V_O$=initial voltage on the energy storage capacitor; and
$\tau$=the time constant of the energy storage capacitor model.

For example, in an actual embodiment of the invention incorporated in a defibrillator, a 34 microfarad energy storage capacitor C was charged to deliver 200 joules at 0° Celsius ($V_O$=3500 volts). Following discharge of the capacitor, the rebound voltage $V_R$ was approximately 18.4 volts and the rebound time $t_R$ approximately 15 seconds. From the measured rebound voltage curve, the component values used to model the dielectric effect in the capacitor may be solved to be $C_d$=0.18 microfarads and $R_d$=8.59 Megohms. Using these values, the rebound voltage at any point in time after discharge of the energy storage capacitor may be estimated. It will be appreciated, however, that the above equations are only a first-order approximation for the rebound voltage.

The rebound phenomenon will be most pronounced when the charging time of the energy storage capacitor is much greater than the time constant $\tau$, and when the discharge time of the capacitor is much less than the time constant $\tau$. Because of the high dielectric constant found in smaller capacitors typically used in portable defibrillators, the rebound voltage is especially pronounced. More generally, it has been observed that an energy storage capacitor in a defibrillator will typically reach a rebound voltage $V_R$ value of approximately 10 to 50 volts in a rebound time $t_R$ of between approximately 5 to 25 seconds, depending on the size of and initial charge on the energy storage capacitor. These ranges are only representative, however, as it will be appreciated that the rebound voltage may fall outside of these ranges depending on the particular application, type of capacitor, size of capacitor, and capacitor charge level.

Figure 4:
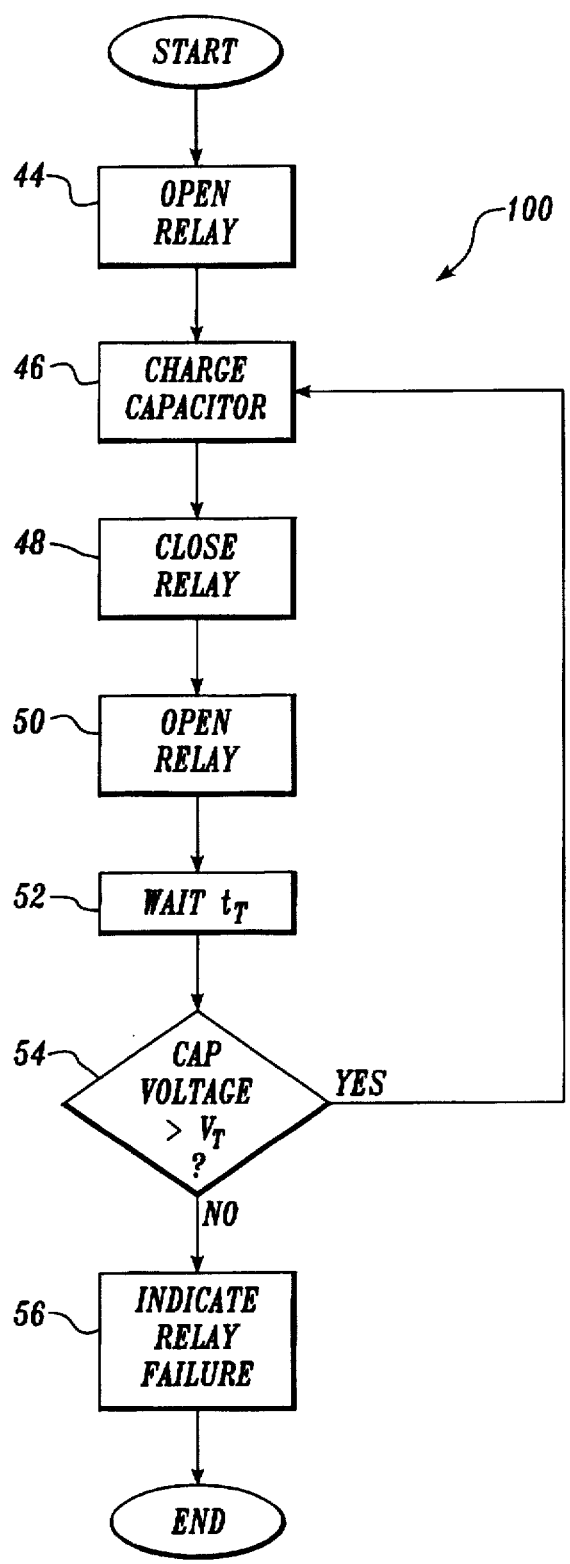
FIG. 4 is a flowchart of a preferred routine for determining whether a relay within the external defibrillator has failed in accordance with the present invention.

The voltage rebound across the energy storage capacitor can be used to detect a failure in the relay 22. To determine whether the relay 22 has failed, the defibrillator 8 includes a method and system for detecting relay failure that relies on the rebound phenomenon illustrated in FIG. 3. A preferred software routine 100 for detecting whether the relay 22 has failed is provided in FIG. 4. As depicted in FIG. 4, at a block 44 a control signal is provided to the relay 22 causing the relay to open. At a block 46, the energy storage capacitor C is charged to a desired voltage for application of a defibrillation pulse. When the voltage on the energy storage capacitor reaches the desired voltage and a defibrillation pulse is to be delivered, at a block 48 a signal is provided to the relay causing the relay to close. The closure of the relay 22 applies a defibrillation pulse to the patient 25. After the application of the defibrillation pulse, at a block 50, a control signal is provided to the relay 22 directing the relay to open. The relay is directed to open to allow the energy storage capacitor to be charged for application of an additional defibrillation pulse.

At a block 52, a predetermined delay time $t_T$ is allowed to elapse. If the relay has opened, during the delay time $t_T$ the voltage will rebound across the energy storage capacitor C as depicted in FIG. 3. If the contacts of the relay 22 become welded shut or otherwise fail by remaining in a conductive state after the command to open the relay 22, the rebound phenomenon illustrated in FIG. 3 will not occur. Rather, the voltage on the energy storage capacitor will remain at a value near or equal to zero volts because the rebound capacitor energy will be shunted to the patient.

At a decision block 54, a test is made of the voltage across the energy storage capacitor C. If the measured voltage across the energy storage capacitor exceeds a threshold voltage $V_T$, the rebound phenomenon is detected. When the rebound voltage is detected, the routine returns to block 46 to allow the energy storage capacitor to be recharged.

Detecting the rebound voltage indicates that the relay has opened correctly. An audible or visual indication may be provided to the defibrillator user to indicate that the relay is operating correctly.

If the voltage across the energy storage capacitor C is below the threshold voltage $V_T$ at decision block 54, the routine continues to a block 56. A measured voltage across the energy storage capacitor less than the threshold voltage $V_T$ indicates that the relay has failed by remaining in the closed (conducting) state. The failure of the relay 22 in the closed state prevents the further charging of the energy storage capacitor C, and prevents additional defibrillation pulses from being delivered to the patient 25. At block 56, the failure of the relay is therefore indicated to the operator of the defibrillator 8. The failure is indicted using an auditory alarm, a visual alarm, or both.

As indicated in FIG. 3, the delay time $t_T$ and threshold voltage $V_T$ are selected to be less than the rebound time $t_R$ and the rebound voltage $V_R$. Selecting a threshold voltage less than the rebound voltage ensures that the correct determination of relay operation is made, since the rebound voltage will vary slightly following each defibrillation pulse. Selecting a delay time less than the rebound time hastens the detection of relay failure. It will be appreciated that the threshold voltage and delay time may be varied depending on the initial charge level of the capacitor, the capacitor size, and other factors. In a preferred embodiment of the invention, the threshold voltage is 5 volts and the delay time is 2 seconds.

While the preferred embodiment of the invention has been illustrated and described, it will be apparent that various changes can be made therein without departing from the spirit and scope of the invention. While developed for use in an external cardiac defibrillator, the method and system for detecting relay failure formed in accordance with the present invention may also be used in technologies unrelated to defibrillators. Any application that requires verifying the operation of a relay that connects a capacitor to a load for delivery of a charge could incorporate the present invention. In different applications, the rebound voltage $V_R$ range and rebound voltage time $t_R$ may vary outside of the approximate ranges disclosed above.

It will also be appreciated that the method and system for detecting relay failure can be practiced with other switching mechanisms or switching circuits other than a relay 22. For example, the method and system for detecting a switch failure is also applicable to a solid state switch used to connect the energy storage capacitor to the patient. The present invention is applicable to any switching mechanism that could fail by remaining in a conductive state.

Those skilled in the art will further recognized that the method and system for detecting relay failure can monitor and identify the occurrence of the rebound voltage phenomenon using methods and systems other than those described above. In the preferred embodiment, a microprocessor 12 is employed to compare the measured voltage with the threshold voltage. However, components other than a microprocessor can be used to compare the measured voltage. For example, a voltage comparator can be provided in lieu of the microprocessor 12 to determine whether the measured voltage is less than or equal to the threshold voltage and, if so, indicate the failure of the relay 22 or other switching mechanism. If a voltage comparator is employed, the delay required before comparing the measured voltage with the threshold voltage can be provided by any one of many conventional delay elements including, for example, a resistor-capacitor circuit. Consequently, within the scope of the appended claims, it will be appreciated that the invention can be practiced otherwise than as specifically described herein.

The embodiments of the invention in which an exclusive property or privilege is claimed are defined as follows:

1. A method of detecting the failure of a relay coupled between an energy storage capacitor and a load following the discharge of a charge stored in the energy storage capacitor into the load by closing the relay, the method comprising the steps of:
   (a) directing the relay to open after the discharge of the energy storage capacitor;
   (b) delaying a period after directing the relay to open so that time is allowed for a rebound voltage to begin developing on the energy storage capacitor;
   (c) measuring a voltage across the energy storage capacitor; and
   (d) comparing the measured voltage with a threshold voltage, the relay having failed in a closed position if the measured voltage does not exceed the threshold voltage.

2. The method of claim 1, wherein the step of comparing the measured voltage with a threshold voltage comprises the steps of:
   (a) scaling the measured voltage to produce a scaled voltage indicative of the measured voltage; and
   (b) comparing the scaled voltage with a scaled threshold voltage.

3. The method of claim 1, wherein the threshold voltage is less than a rebound voltage of the energy storage capacitor.

4. The method of claim 3, wherein the rebound voltage falls within a range of approximately 10 to 50 volts.

5. The method of claim 1, further comprising the step of indicating to a defibrillator operator the relay failure when the measured voltage is less than or equal to the threshold voltage.

6. The method of claim 1, further comprising the step of indicating to a defibrillator operator that the relay is operating when the measured voltage exceeds the threshold voltage.

7. A system for determining when a relay coupled between an energy storage capacitor and a load has failed during discharge of the energy storage capacitor into the load, the energy storage capacitor coupled to a charging circuit to allow the capacitor to be charged when the relay is open, the system comprising:
   (a) a control circuit for generating a control signal directing the relay to open after the energy storage capacitor has been discharged;
   (b) a monitor circuit coupled to the energy storage capacitor for measuring the voltage across the energy storage capacitor and producing a signal indicative of the voltage across the energy storage capacitor; and
   (c) a comparator coupled to the control circuit and the monitor circuit and receiving the signal indicative of the voltage across the energy storage capacitor, the comparator comparing the voltage across the energy storage capacitor with a threshold voltage at a predetermined time after the relay has been directed to open, the predetermined time being long enough to allow a rebound voltage to begin developing on the energy storage capacitor, and generating a failure signal if the voltage across the energy storage capacitor does not exceed the threshold voltage.

8. The system of claim 7, wherein the monitor circuit includes a voltage divider coupled to the energy storage capacitor for scaling the voltage across the energy storage capacitor to produce the signal indicative of the voltage across the energy storage capacitor.

9. The system of claim 8, wherein the monitor circuit includes an amplifier coupled to the voltage divider for amplifying the signal indicative of the voltage across the energy storage capacitor.

10. The system of claim 7, wherein the comparator comprises:

(a) an analog-to-digital converter coupled to the monitor circuit and converting the signal indicative of the voltage across the energy storage capacitor into a measured voltage level; and (b) a microprocessor coupled to the analog-to-digital converter for comparing the measured voltage level with the threshold voltage and generating the failure signal if the measured voltage level does not exceed the threshold voltage.

11. The system of claim 7, wherein the threshold voltage is less than a rebound voltage of the energy storage capacitor.

12. The system of claim 11, wherein the rebound voltage falls within a range of approximately 10 to 50 volts.

13. The system of claim 7, wherein the failure signal is an audible alarm.

14. The system of claim 7, wherein the failure signal is a visual alarm.

15. A method for detecting the failure of a relay in a defibrillator following the discharge of an energy storage device in the defibrillator, the method comprising the steps of:

(a) closing the relay so as to cause the discharge of the energy storage device;

(b) directing the relay to open after the discharge of the energy storage device;

(c) waiting a period after the discharge of the energy storage device, the waiting period being long enough for a rebound voltage to begin developing across the energy storage device to a level that is in excess of a first threshold voltage;

(d) measuring a voltage on the energy storage device; and (e) comparing the measured voltage to a second threshold voltage less than or equal to the first to determine if the relay has failed.

16. The method of claim 15, wherein the rebound voltage falls within a range of approximately 10 to 50 volts.

17. The method of claim 15, further comprising the step of indicating to a defibrillator operator the relay failure when the measured voltage is less than or equal to the second threshold voltage.

18. The method of claim 15, further comprising the step of indicating to a defibrillator operator that the relay is operating when the measured voltage exceeds the second threshold voltage.

19. The method of claim 15, wherein the second threshold voltage is set at approximately 5 or more volts.

20. The method of claim 15, wherein the waiting period is approximately 2 or more seconds.

* * * * *